United States Patent [19]
Fujii

[11] Patent Number: 4,864,059
[45] Date of Patent: Sep. 5, 1989

[54] PROCESS FOR PRODUCING UREA

[75] Inventor: Hidetsugu Fujii, Chiba, Japan

[73] Assignee: Toyo Engineering Corporation, Tokyo, Japan

[21] Appl. No.: 782,854

[22] Filed: Oct. 2, 1985

[30] Foreign Application Priority Data

Nov. 2, 1984 [JP] Japan .................. 59-232135

[51] Int. Cl.$^4$ .................. C07C 126/02
[52] U.S. Cl. .................. 564/71; 564/72
[58] Field of Search .................. 564/71, 72

[56] References Cited

U.S. PATENT DOCUMENTS

| | | | |
|---|---|---|---|
| 3,984,469 | 10/1976 | Guadalupi et al. | 564/72 |
| 4,137,272 | 1/1979 | Guadalupi et al. | 564/72 |
| 4,314,077 | 2/1982 | Zardi et al. | 564/72 |
| 4,500,734 | 2/1985 | Lagana et al. | 564/72 |
| 4,540,813 | 9/1985 | van Nassau et al. | 564/71 |

Primary Examiner—Charles F. Warren
Assistant Examiner—Carolyn S. Greason
Attorney, Agent, or Firm—Flynn, Thiel, Boutell & Tanis

[57] ABSTRACT

Disclosed herein is a method of utilizing inert gases, which are introduced as impurities in the feed raw materials for the synthesis of urea and also as an anti-corrosion agent into a urea process, as a stripping agent of unreacted materials in one or more of the below-mentioned separation steps, in a urea process in which: urea is synthesized from ammonia and carbon dioxide in the presence of an excess ammonia; unreacted materials including the excess ammonia are separated from the resulting urea synthesis solution as gaseous mixtures of ammonia and carbon dioxide successively at a plurality of pressure levels; the gaseous mixtures thus-separated are absorbed in solvents or condensed at the corresponding pressure levels; and the solutions or condensates thus-formed are circulated to the urea synthesis step.

By this method, the separation efficiency of the unreacted materials is improved in the lower pressure separation steps, which eventually results in the improvement in the unit consumption of steam and the size reduction in some of the lower pressure equipments in the urea process.

5 Claims, 1 Drawing Sheet

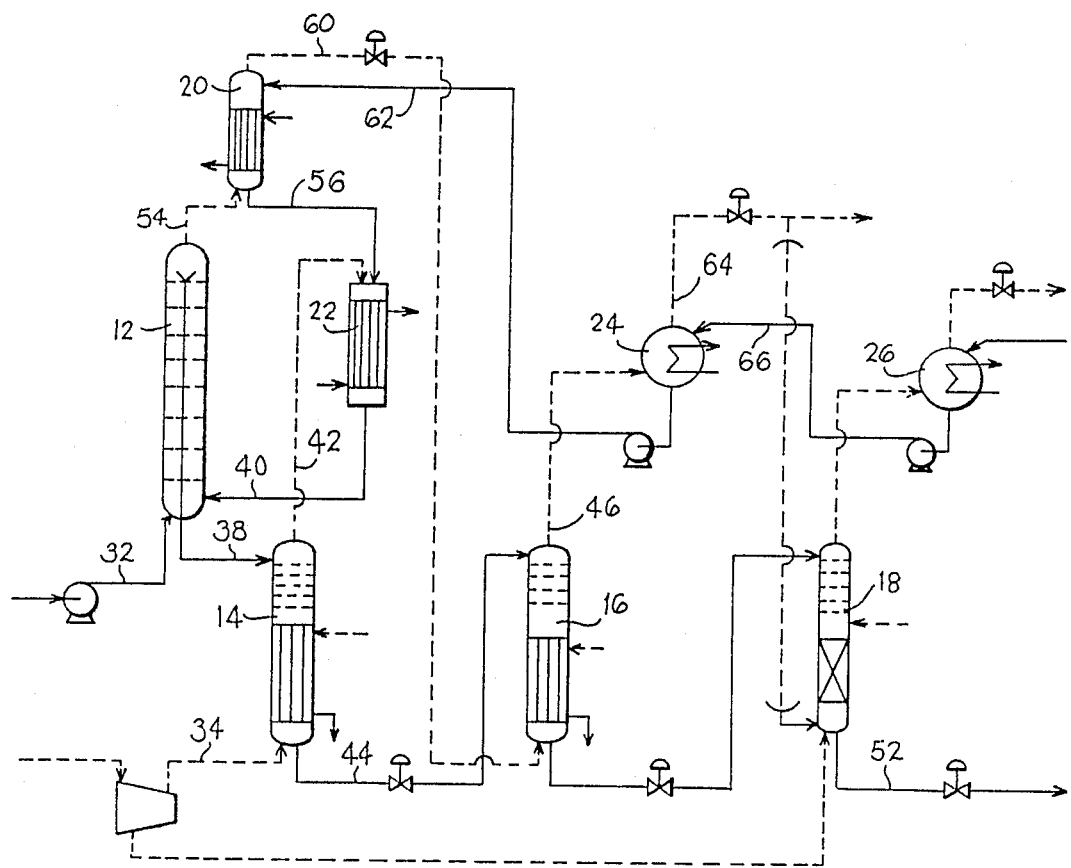

PROCESS FOR PRODUCING UREA

FIELD OF THE INVENTION

This invention relates to a process for producing urea. More specifically, in a process for producing urea in which: urea is synthesized from ammonia and carbon dioxide in the presence of excess ammonia; unconverted materials including the excess ammonia are separated from the resulting urea synthesis solution as gaseous mixtures of ammonia and carbon dioxide successively at a plurality of pressure levels; the gaseous mixtures thus-separated are absorbed in solvents or condensed at the corresponding pressure levels; and the solutions or condensates thus-formed are circulated to the urea synthesis step, this invention relates to a method of utilizing inert gases introduced into the process as a stripping agent in one or more of said separation steps.

DESCRIPTION OF THE PRIOR ART

In the field of urea production processes, the prevalent process scheme is changing from the conventional solution recycle process to the so-called stripping process. Specifically, since the urea synthesis solution withdrawn from a urea synthesis reactor contains unconverted ammonium carbamate and excess ammonia (these components are hereinafter simply referred to as unreacted materials) in addition to urea, these unreacted materials are subjected to those steps of separation (precisely speaking, the decomposition reaction of ammonium carbamate occurs prior to the separation of the unreacted materials, but the decomposition reaction and the separation are collectively referred to as separation for the sake of brevity), recovery and recycle to the synthesis step. In the stripping process, the separation of unreacted materials is carried out by using feed carbon dioxide or ammonia as a stripping agent just like the air used in the aeration method to separate more unreacted materials as a gaseous mixture of ammonia and carbon dioxide than in the case of using only heat for effecting the separation.

The pressure in effecting the stripping is generally a substantially equal pressure to the urea synthesis pressure (hereinafter, the expression "the same pressure" signifies "a substantially equal pressure" and also the expression "the same" regarding to pressure means "substantially equal"). The reason for effecting the separation at such a high pressure is to recover the heat generated by absorbing or condensing the thus-separated gaseous mixture as steam or a direct heat source for heating streams in the urea process at a highest possible temperature level. Accordingly, although the stripping process appears at a glance to be effected only for the purpose of separating the unreacted materials, it also intends to make the heat recovery at high temperatures (or high pressures) practicable. A certain urea process employs the stripping in the separation step of a lower pressure than in the synthesis step with the aim being other than heat recovery.

On the other hand, feed gaseous carbon dioxide contains primarily 0.5% by volume or more of hydrogen and additionally, fragments of carbon monoxide, methane and the like as its impurities. Further, feed liquid ammonia also contains 0.1-1.0 Nm$^3$ of hydrogen and nitrogen per ton of ammonia in the dissolved form. Being inactive for the urea synthesis reaction, these gases are commonly called inert gases. Thus, these inert gases are inevitably introduced into the urea production process.

Further, 2,000-10,000 ppm by volume of oxygen relative to the feed carbon dioxide is generally introduced into any or all of the urea synthesis reactor, the stripper in which stripping of unreacted materials is carried out and the carbamate condenser in which the gases thus-stripped are absorbed or condensed, with a view toward preventing the materials of these equipments from being corroded. The oxygen is generally introduced thereinto as air, although it is also proposed to be introduced in the form of pure oxygen or an oxygen-enriched gas.

The method of introducing air into the process is to add it previously to the feed gaseous carbon dioxide but the air may in some cases be introduced directly into the intended equipments after being pressurized separately. Thus, these inert gases (the air added for the purpose of corrosion prevention as well as the inert gases originated from the feed ammonia and carbon dioxide are simply called "inert gases" hereunder) amount to 350-1,000 Nm$^3$/hour in a urea plant having a production capacity of 1,000 tons per day of urea.

The greater part of the inert gases introduced into the process are withdrawn from the top of the urea synthesis reactor or from the carbamate condenser. In this occasion, the inert gases are accompanied by ammonia and carbon dioxide. These useful gases have conventionally been washed and recovered at the synthesis pressure or a lower pressure than that so as to discharge the inert gases to the outside of the process. The heat generated by the absorption of ammonia and carbon dioxide in said washing and recovery step has generally been utilized in an effective manner within the process.

The treatment of the inert gases within the process in such a manner is likely to be rational, but is found to still involve some irrationality as a result of a mature consideration. Namely, the inert gases removed with ammonia and carbon dioxide inherently act as a very useful stripping agent viewed from another angle. From the standpoint of stripping effect alone, it is naturally desired to use a gas other than ammonia and carbon dioxide. This is because the amount of unreacted materials remaining in the urea synthesis solution withdrawn from the stripper can theoretically be reduced to substancially zero by stripping them using such a gas as a stripping agent, assuming that there are no increases in the hydrolysis of urea and the formation of biuret during the stripping operation. Thus, stripping processes using a large amount of air or ammonia synthesis gas have already been proposed. However, these processes have never been practiced because the absorption or condensation of the ammonia and carbon dioxide separated by the stripping using such a gas as a stripping agent has to be effected at a low temperature, thereby causing a heat recovery of good quality to be impracticable.

On the other side, in the stripping process using carbon dioxide as the stripping agent, the urea synthesis conditions are being changed gradually from the synthesis using a small exess of ammonia to the synthesis using a larger excess of ammonia. This is because the conversion rate to urea is high and therefore the consumption of steam for separating unreacted materials is reduced in the synthesis using excess ammonia. However, as the amount of excess ammonia increases, the stripping using carbon dioxide as the stripping agent will have to be carried out under increasingly difficult conditions. If the stripping is forcedly effected under such severe conditions, it will cause the hydrolysis of urea and the formation of biuret to increase and further will raise a fear of corrosion of the equipments on account of the higher temperature operation. Accordingly, in the stripping process in which the urea synthesis is carried out using a large excess of ammonia (the molar ratio of ammonia to carbon dioxide is approximately 3.3 or more), a separation-absorption operation is incorporated into the process at a so-called medium pressure level (about 15–25 atmospheres), thereby controlling the amount of unreacted materials to be separated by the stripping under the urea synthesis pressure.

Further, the difficulty of separating unreacted materials due to the presence of a large excess of ammonia extends to the separation-absorption operation at the medium and low pressure levels, though not so serious as that under the synthesis pressure. In order to improve this situation, it may be considered to use carbon dioxide as a stripping agent in the separation at these pressure levels. However, as its pressure decreases, heat recovery in the absorption step is rendered difficult and thus the process becomes uneconomical.

In view of the above-described state of the art, it will be understood that the problems to be solved lie in how the aforesaid unfavorable effect can be reduced in the stripping process in which a large excess of ammonia is used in the synthesis of urea and how it is performed at as high a pressure as possible. More particularly, from the consideration of the improvement of separation efficiency of unreacted materials, the operability of the separation-absorption steps and further the effect of these factors on the whole urea process, it was found to be desirable that the amount of unreacted materials remaining in the urea synthesis solution after the separation of unreacted materials at each pressure level was reduced by about 15% or more as compared with the prior art manner. For example, when the unreacted material is supposed to remain in the synthesis solution after the medium pressure separation in an amount of 10–15% by weight, it is desirable to reduce this remaining amount by 1.5–2.25% by weight or more.

It is very difficult to reduce the remaining unreacted materials in the synthesis solution withdrawn from the stripping step under the synthesis pressure. Therefore, the remaining unreacted materials have to be removed in other separation steps. However, another problem will in some cases arise depending on the procedure employed in the separation steps. The most easy procedure is to raise the temperature if the pressure remains unchanged. However, this procedure undesirably gives rise to the corrosion of the equipments as well as the increase in the hydrolysis of urea and the formation of biuret. Here, the present inventors have come to the thought of utilizing the aforesaid inert gases as a stripping agent. Namely, as a result of an examination and test, the amount of inert gases introduced into the process was found to be most suitable for the reduction of the unreacted materials remaining to the aforesaid extent in the synthesis solution and also to be a proper amount which does not interfere with the subsequent absorption step. Thus, the invention hereinafter described has been completed on the basis of this discovery.

SUMMARY OF THE INVENTION

In a urea synthesis process which comprises: synthesizing urea from ammonia and carbon dioxide as starting materials in the presence of excess ammonia; subjecting the urea synthesis solution thus-formed to stripping under a high pressure using the carbon dioxide or ammonia as a stripping agent and subjecting the resulting urea synthesis solution to at least one stage of decomposition and separation operation under a lower pressure than the synthesis pressure in order to separate the excess ammonia and the ammonia and carbon dioxide formed by the decomposition of ammonium carbamate which has not been converted to urea from the urea synthesis solution, subjecting the thus-formed gaseous mixtures of ammonia and carbon dioxide to absorption in solvents or condensation; and recycling the thus-formed solutions or condensates to the urea synthesis step, the present invention provides an improvement of said urea synthesis process which comprises: withdrawing inert gases introduced into the process which are inactive for the urea synthesis reaction at a site where they are accumulated; and utilizing the inert gases thus-withdrawn as a stripping agent of the unreacted materials in at least one stage of the separation operation at the lower pressure.

BRIEF DESCRIPTION OF THE DRAWING

The drawing schematic flow diagram illustrating an example of the embodiments of the present invention. The solid lines signify that the fluid flowing therethrough is a liquid, while the dotted lines signify that it is a gas. The following reference numerals indentify the respective items of equipment that follow them. 12—Synthesis reactor, 14—Stripper, 16—Medium pressure decomposer, 18—Low pressure decomposer, 20—High pressure washing column, 22—Carbamate condenser, 24—Medium pressure absorber, 26—Low pressure absorber, and 32 and above—Conduits for process fluids.

In order to facilitate better and concrete understanding, the present invention is illustrated below by reference to the drawings regarding a standard stripping process in which a large excess of ammonia is used for the synthesis of urea. In the carbon dioxide stripping process, the urea synthesis is carried out under the conditions of a pressure of 140–220 atm., a temperature of 180°–200° C. and an ammonia to carbon dioxide molar ratio of 2.3–5.0 including the unreacted materials recycled to the synthesis step. In general, the higher the molar ratio in said range, the higher will be the synthesis pressure. Further, the rate of conversion of carbon dioxide to urea will also be increased from 55% to 75%.

The urea synthesis solution thus-obtained is conducted via a conduit 38 to the top of the stripper 14 where it is subjected to stripping by a feed carbon dioxide gas fed through a conduit 34. By the stripping, the greater part of the unreacted materials in the synthesis solution is separated as a gaseous mixture of ammonia and carbon dioxide. The pressure in the stripper 14 is generally the same pressure as in the synthesis. Inert gases in the aforesaid feed carbon dioxide also flows upwards through the stripper and is conducted to a carbamate condenser 22 via a conduit 42 together with a gaseous mixture of ammonia and carbon dioxide separated in the stripper and the feed carbon dioxide gas. In this condenser 22, a part of the ammonia and carbon dioxide is absorbed into an aqueous carbamate solution fed through a conduit 56 from a high-pressure washing column 20 for washing the inert gas under the same pressure as the synthesis pressure. The heat of absorption generated in the carbamate condenser 22 is recovered as a steam and utilized effectively within the process.

The thus-formed concentrated carbamate solution, unabsorbed gaseous ammonia, carbon dioxide and inert gases are recycled to the bottom of a synthesis reactor 12 via a conduit 40. Further, hydrogen and nitrogen dissolved in a feed liquid ammonia supplied through a conduit 32 is also introduced into the synthesis reactor 12. The inert gases thus-introduced into the synthesis reactor 12 are withdrawn from the reactor at its top, accompanied by ammonia and carbon dioxide in amounts depending on the synthesis conditions. The content of these gases reaches at most 90% by volume.

Then, in the present invention, (1) a gaseous mixture of ammonia, carbon dioxide and inert gases is conducted via a conduit 54 to a high-pressure washing column 20 operated under the same pressure where the greater part of the ammonia and carbon dioxide contained therein is washed and the content of these gases in the thus-washed gaseous mixture is thereby reduced to 40% by volume or less. The heat of absorption thus-generated is recovered to be utilized effectively within the process.

On the other side, the urea synthesis solution which has been reduced in the content of unreacted materials to 20–30% by weight by the carbon dioxide stripping is lowered in pressure to 15–25 atm. via a conduit 44 and fed to a medium pressure decomposer 16 where it is subjected to a medium pressure separation operation. The separation has been carried out by heating as well as flashing through depressurization. In the present invention, however, (2) the separation is effected by introducing the inert gases, which have been washed in the high pressure washing column 20 and reduced in pressure, via conduit 60 into the bottom of the medium pressure decomposer 16 as a stripping agent concurrently with or subsequent to said heating so as to reduce the unreacted materials remaining in the urea synthesis solution to a greater extent than in the conventional manner. By this stripping, the amount of unreacted materials remaining in the synthesis solution is reduced by 15% by weight as compared with that in the conventional manner. For example, if the unreacted materials are conventionally supposed to remain in an amount of 8% by weight, they will be reduced to 6.8% by weight or less by the application of the present invention. When the stripping is performed concurrently with the heating, the heater may preferably be of a falling-film type since the heating has to be effected in a short period of time.

A gaseous mixture consisting of the ammonia and carbon dioxide separated by this operation and the inert gases is conducted from the top of the decomposer 16 through a conduit 46 to a medium pressure absorber 24 oparated under the same pressure as in the decomposer 16. Ammonia and carbon dioxide in the gaseous mixture are absorbed into a carbamate solution fed from a low pressure absorber 26 via a conduit 66. The inert gases after the absorption are washed with water to remove ammonia and carbon dioxide still contained therein in accordance with the degree of their existence. The heat of absorption generated in the absorber 24 is utilized for the vaporization of water in a urea concentration step.

The inert gases flowing through a conduit 64 after the absorption or the washing are subjected to a proper treatment as required and thereafter discharged to the outside of the process or (3) further utilized for the stripping in a low pressure decomposer 18 in accordance with the present invention. The stripping procedure is similar to that of the medium pressure decomposer 16 and the treatment of gaseous mixture after the stripping is also similar to that of the medium pressure absorber 24. Thus, the unreacted materials remaining in the urea synthesis solution at the outlet of the low pressure decomposer 18 or in a conduit 52 is also reduced in amounts to a minimum. Incidentally, the carbon dioxide stripping conventionally utilized in the low pressure separation step may also be used concurrently with this inert gas stripping.

Explained above is the case in which urea is synthesized using excess ammonia, the resulting urea synthesis solution is subjected to stripping using carbon dioxide as a stripping agent, and the inert gases are withdrawn from the urea synthesis reactor. However, it is also feasible to apply the present invention to the case in which ammonia is used as the stripping agent or the inert gases are withdrawn from the carbamate condenser. It is further feasible to apply the present invention with similar effects to the stripping process in which urea is synthesized using a small excess of ammonia. Specifically, in this case, the inert gases withdrawn from the high pressure washing column 20 is directly introduced into the low pressure separation step to be used as a stripping agent.

In any case, the inert gases per se introduced into the process and the amounts thereof are adequate for the application of the present invention to further reducing the remaining unreacted materials in the separation steps subsequent to the high-pressure stripping. In this sense, the scope of the present invention is not limited to the stripping process. Namely, in the conventional solution recycle process, the inert gases are discharged from the medium pressure absorber by way of the urea synthesis reactor and the medium pressure decomposer to the outside of the proces. The inert gases may instead be utilized as a stripping agent in the low pressure separation step to produce the effect of the present invention.

As is obvious from the foregoing description, the following effects are produced by the application of the present invention.

(1) The improved separation efficiency in the medium pressure separation step permits the amount of water required as a solvent in the absorption step to be reduced, thus resulting in the improvements of the conversion rate to urea and the consumption of steam.

(2) The improved separation efficiency in the medium pressure separation step permits the size of the low pressure absorption unit to be minimized. Further, when the present invention is applied to the low pressure separation step, the amount of ammonia and carbon dioxide contained in the water vapor from the urea concentration step is reduced so that the equipments required for the recovery of these components is made smaller and the utilities thereby required are also reduced.

(3) In the present invention, since oxygen is inevitably introduced into the medium pressure decomposer, no special equipments (such as compressor) are required for the supply of oxygen even if the decomposer is composed of materials which need anti-corrosion oxygen. Alternatively, the quality of the materials can be degraded.

The present invention is illustrated specifically and numerically in the application and effects thereof by the following example.

EXAMPLE

A preferred exemplary embodiment of the present invention is illustrated by reference to the drawing. In the following description, the excess ammonia and unreacted ammonium carbamate are computed in terms of ammonia and carbon dioxide.

In a stripping process having a capacity of producing 600 tons per day of urea in which urea was synthesized using a large excess of ammonia and the resulting urea synthesis solution was subjected to stripping using carbon dioxide as a stripping agent, a synthesis solution containing 610 tons/day of urea, 674 tons/day of ammonia, 211 tons/day of carbon dioxide and 348 tons/day of water was withdrawn from a urea synthesis reactor 12 operated under the conditions of a pressure of 175 atm., a temperature of 190° C. and an ammonia to carbon dioxide molar ratio of 4.0 and was then fed to a stripper 14 operated under the same pressure. 440 tons/day of fresh feed carbon dioxide gas was blown into the bottom of a heater of the stripper 14 through a conduit 34 as a stripping agent. The carbon dioxide gas primarily contained 2.0% by volume of hydrogen as impurities and was added with 230 Nm$^3$/hour of air to have 5,000 ppm by volume of oxygen relative to the carbon dioxide for the purpose of preventing the equipments from being corroded.

In the stripper 14, 525 tons/day of ammonia, 487 tons/day of carbon dioxide and 47 tons/day of water were separated as a gaseous mixture thereof with a carbon dioxide gas fed through a conduit 34 by a combined action of the heating by a high pressure steam and the carbon dioxide stripping. Further, the urea synthesis solution withdrawn from the bottom of the stripper 14 via a conduit 44 after being subjected to the stripping contained 608, 150, 165 and 300 tons per day of urea, ammonia, carbon dioxide and water, respectively.

The gaseous mixture flowing through a conduit 42 was conducted to a carbamate condenser 22 operated under the same pressure as in the stripping where approximately 60% by weight of the ammonia and carbon dioxide contained therein were absorbed at 180° C. into an aqueous carbamate solution passed from the high pressure washing column 20. The resulting solution was circulated together with the remaining about 40% by weight of unabsorbed gases and the inert gases to the bottom of the synthesis reactor 12 via a conduit 40. The heat generated in the condenser 22 was recovered as steam and utilized effectively in other steps within the process.

The inert gases that flowed into the synthesis reactor 12 were accumulated at the top portion of the reactor together with 3 Nm$^3$/hour of other inert gases consisting primarily of hydrogen and nitrogen previously contained in a fresh feed liquid ammonia fed through a conduit 32. The resulting inert gases, withdrawn from the reactor via a conduit 54 without being reduced in pressure, were accompanied by a gaseous mixture of 76 tons/day of ammonia, 25 tons/day of carbon dioxide and 7 tons/day of water. The greater part of the gaseous mixture was absorbed at the high pressure washing column 20 into an aqueous carbamate solution fed through a conduit 62 from a medium pressure absorber 24 described below. Ammonia, carbon dioxide and water in the inert gases were reduced in amounts to 15, 3, and 1 ton/day respectively, and thus the gaseous mixture leaving the high pressure washing column 20 was composed primarily of the inert gases.

The inert gases flowing through a conduit 60 was reduced in pressure to 18 atm. and then conducted to the bottom of a heater of a medium pressure decomposer 16 described below in accordance with the present invention. On the other hand, the urea synthesis solution withdrawn from the stripper 14 was also reduced in pressure to 18 atm. and fed to the top of the trays in the medium pressure decomposer 16 via a conduit 44. During the subsequent descending through the decomposer, the synthesis solution was subjected to a combined action of the heating by a high pressure steam and the stripping by the inert gases fed below said heating section through a conduit 60 to separate ammonia, carbon dioxide and water therefrom. The urea synthesis solution discharged from the bottom (160° C.) of the medium pressure decomposer 16 through a conduit 48 contained 606 tons/day of urea, 51 tons/day of ammonia, 20 tons/day of carbon dioxide and 266 tons/day of water.

A gaseous mixture comprising the ammonia, carbon dioxide and water thus-separated and the inert gases withdrawn from the top of the decomposer 16 was conducted via a conduit 46 to a medium pressure absorber 24 operated under the same pressure as in the decomposer 16 in which absorbed other gaseous components than the inert gases were almost completely absorbed at 110° C. into an aqueous carbamate solution fed through a conduit 66 from a low pressure absorber 26. The resulting inert gases containing a fragment of ammonia and carbon dioxide were withdrawn from the top of the absorber 24 to be subjected to other treatment. On the other side, the urea synthesis solution flowing through a conduit 48 was depressurized and conducted to a low pressure decomposer 18 where it is separated with the unreacted materials contained therein and thereafter fed to a finishing step.

The results are summarized as follows in comparison with those obtained prior to the application of the present invention, - that is: the amount of ammonia and carbon dioxide in the urea synthesis solution flowing through the conduit 48 was reduced by 25% by weight; the equipments for the low pressure decomposition and absorption steps were made smaller in size; the amount of aqueous carbamate solution flowing through the conduit 66 was reduced by 20% by weight and therefore the amount of water introduced into the synthesis reactor was reduced, with the result that the rate of conversion to urea was improved to eventually reduce the steam consumption of the urea process by 40 kg per ton of urea; and the unnecessity of compressing anti-corrsion air to be supplied to the medium pressure decomposer 16 permitted the power consumption of the process to be saved by 0.46 kwh per ton of urea.

What is claimed is:

1. In a urea synthesis process which comprises reacting carbon dioxide and an excess of ammonia in a reactor, at an elevated temperature and pressure, whereby to form urea, removing from the bottom of the reactor a first urea synthesis liquid stream comprised of urea and unreacted materials dissolved in water, and simultaneously removing from the top of the reactor a first effluent gas stream comprising ammonia, carbon dioxide, water vapor and inert gases; flowing said first urea synthesis liquid stream through a stripping zone which is at substantially the same pressure as said reactor and, in said stripping zone, contacting said first liquid stream with carbon dioxide gas or ammonia gas to separate a second effluent gas stream comprising ammonia and carbon dioxide and to simultaneously produce a second urea synthesis liquid stream comprising urea and a reduced amount of the unreacted materials dissolved in water; washing said first effluent gas stream, in a high pressure washing column which is at substantially the same pressure as said reactor, with an aqueous carbamate solution whereby to produce a liquid aqueous carbamate solution and a third effluent gas stream containing less than 40 vol. % of ammonia and carbon dioxide and the balance consisting essentially of inert gases; contacting said second effluent gas stream with said liquid aqueous carbamate solution at substantially the same pressure as in said reactor, recovering a concentrated aqueous carbamate solution containing ammonia and carbon dioxide and recycling said concentrated carbamate solution to said reactor; feeding said second urea synthesis liquid stream to a decomposer which is at a lower pressure than the pressure in said reactor and contacting same with said third effluent gas stream whereby to strip ammonia and carbon dioxide from said second liquid stream to recover a third urea synthesis liquid stream containing a lower amount of ammonia and carbon dioxide than said second liquid stream; condensing or absorbing in an aqueous solution the ammonia and carbon dioxide that were stripped from said second liquid stream and recycling the thus-formed condensate or solution to said high pressure washing column as said aqueous carbamate solution therein.

2. A urea synthesis process as claimed in claim 1 in which, in said reactor, the pressure is from 140 to 220 atmospheres, the temperature is from 180° to 200° C. and the mole ratio of ammonia to carbon dioxide is from 2.3 to 5.0.

3. A urea synthesis process as claimed in claim 1 in which, in said stripping zone, said first liquid stream is contacted with carbon dioxide gas.

4. In a urea synthesis process which comprises reacting carbon dioxide and an excess of ammonia in a reactor, at an elevated temperature and pressure, whereby to form urea, removing from the bottom of the reactor a first urea synthesis liquid stream comprised of urea and unreacted materials dissolved in water, and simultaneously removing from the top of the reactor a first effluent gas stream comprising ammonia, carbon dioxide, water vapor and inert gases; flowing said first urea synthesis liquid stream through a stripping zone which is at substantially the same pressure as said reactor and, in said stripping zone, contacting said first liquid stream with carbon dioxide gas or ammonia gas to separate a second effluent gas stream comprising ammonia and carbon dioxide and to simultaneously produced a second urea synthesis liquid stream comprising urea and a reduced amount of the unreacted materials dissolved in water; washing said first effluent gas stream, in a high pressure washing column which is at substantially the same pressure as said reactor, with an aqueous carbamate solution whereby to produce a liquid aqueous carbamate solution and a third effluent gas stream containing less than 40 vol. % of ammonia and carbon dioxide and the balance consisting essentially of inert gases; contacting said second effluent gas stream with said liquid aqueous carbamate solution at substantially the same pressure as in said reactor, recovering a concentrated aqueous carbamate solution containing ammonia and carbon dioxide and recycling said concentrated carbamate solution to said reactor; reducing the pressure of said second urea synthesis liquid stream and then feeding said second urea synthesis liquid stream to a medium pressure decomposer which is at a lower pressure than the pressure in said reactor, reducing the pressure of said third effluent gas stream and then feeding said third effluent gas stream to said medium pressure decomposer and therein contacting it with said second urea synthesis liquid stream to strip ammonia and carbon dioxide therefrom to produce a fourth effluent gas stream and recovering a third urea synthesis liquid stream having a reduced content of ammonia and carbon dioxide, contacting said fourth effluent gas stream with an aqueous solution to absorb ammonia and carbon dioxide in said aqueous solution and to discharge a fifth effluent gas stream, and recycling said aqueous solution to said high pressure washing column as said aqueous carbamate solution therein.

5. A urea synthesis process as claimed in claim 4 in which the pressure of said third urea synthesis liquid stream is reduced and then said third liquid stream is fed to a low pressure decomposer which is at a lower pressure than the pressure in said medium pressure decomposer, the pressure of said fifth effluent gas stream is reduced and then said fifth effluent gas stream is fed to said low pressure decomposer wherein it contacts said third liquid stream to strip ammonia and carbon dioxide therefrom.

* * * * *